US00PP23470P3

(12) United States Plant Patent

Klemm et al.

(10) Patent No.: US PP23,470 P3

(45) Date of Patent: Mar. 12, 2013

(54) *CALIBRACHOA* PLANT NAMED 'KLECA09210'

(50) Latin Name: ***Calibrachoa* hybrid**
Varietal Denomination: KLECA09210

(75) Inventors: Nils Klemm, Stuttgart (DE); Anita Stoever, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 348 days.

(21) Appl. No.: 12/661,881

(22) Filed: Mar. 25, 2010

(65) Prior Publication Data

US 2011/0239344 P1 Sep. 29, 2011

(51) Int. Cl.
*A01H 5/00* (2006.01)

(52) U.S. Cl. ..... Plt./413

(58) Field of Classification Search ..... Plt./413
See application file for complete search history.

(56) References Cited

PUBLICATIONS

UPOV ROM GTITM Computer Database, GTI Jouve Retrieval Software 2011/03 Citation for 'KLECA09210'.*
Anonymous. 2012 Selecta Catalog, particularly pp. 18-61. Accessed Jul. 12, 2011.*
Pluto no PBR Citation for 'KLECA09210' Nov. 15, 2010.*

* cited by examiner

*Primary Examiner* — Wendy C Haas
(74) *Attorney, Agent, or Firm* — Jondle & Associates, P.C.

(57) ABSTRACT

A new *Calibrachoa* plant named 'KLECA09210' particularly distinguished by its single, purple flowers, and a semi-trailing form and growth habit, is disclosed.

1 Drawing Sheet

Genus and species: *Calibrachoa* hybrid.
Variety denomination: 'KLECA09210'.

BACKGROUND OF THE NEW PLANT

The present invention comprises a new and distinct variety of *Calibrachoa*, botanically known as *Calibrachoa* hybrid and hereinafter referred to by the variety name 'KLECA09210'. The new variety originated from an open pollination made in June 2006 in Stuttgart, Germany. The female parent was the proprietary *Calibrachoa* plant 'CA060011' (unpatented), while the male parent was an unknown individual *Calibrachoa* plant.

The new variety was first propagated via vegetative cuttings in May 2007 in Stuttgart, Germany and has been asexually reproduced by vegetative cuttings and in-vitro propagation by tissue culture of shoot tips in Stuttgart, Germany for more than 30 generations. The present invention has been found to retain its distinctive characteristics through successive asexual propagations.

'KLECA09210' has not been made publicly available or sold more than one year prior to the filing date of this application.

SUMMARY OF THE INVENTION

The following are the most outstanding and distinguishing characteristics of this new variety when grown under normal horticultural practices in Stuttgart, Germany.

1. Single, purple flowers; and
2. A semi-trailing form and growth habit.

DESCRIPTION OF THE PHOTOGRAPH

This new *Calibrachoa* plant is illustrated by the accompanying photographs which show flowers and foliage of the plant. The colors shown are as true as can be reasonably obtained by conventional photographic procedures. The photographs were taken in May 2009 of a 5-month-old *Calibrachoa* plant; grown in a glass greenhouse in Stuttgart, Germany.

DESCRIPTION OF THE NEW VARIETY

Figure 1:
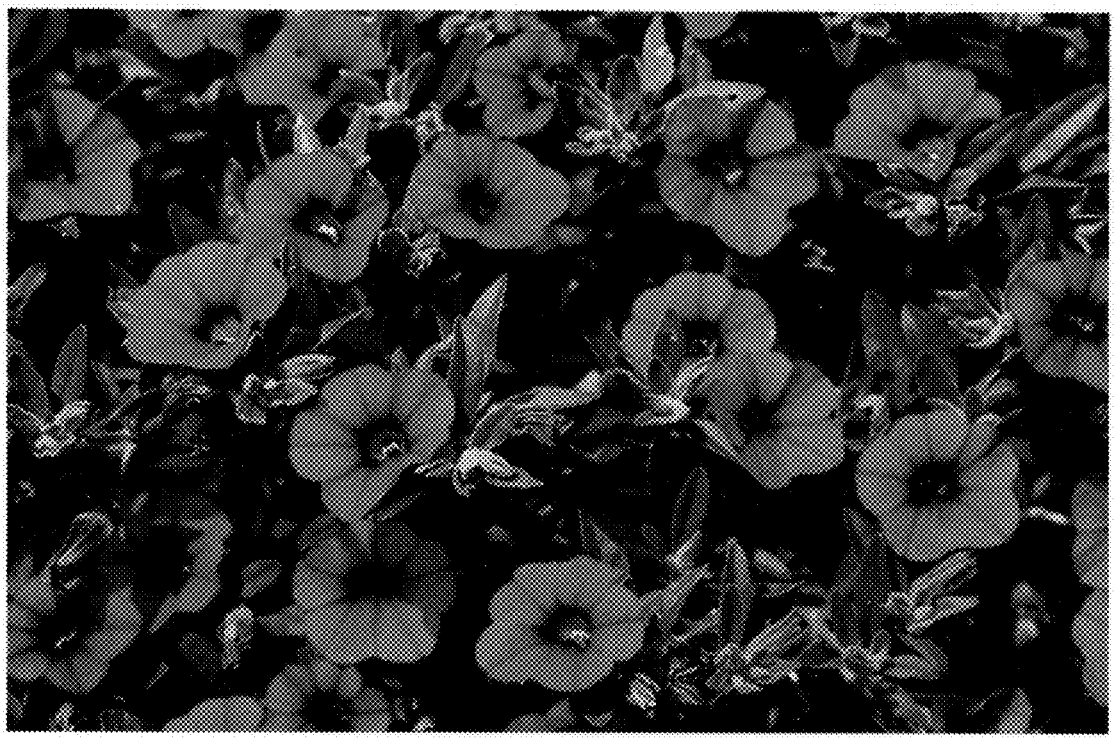
FIG. 1 shows the flowers and foliage at various stages of development.
Figure 2:
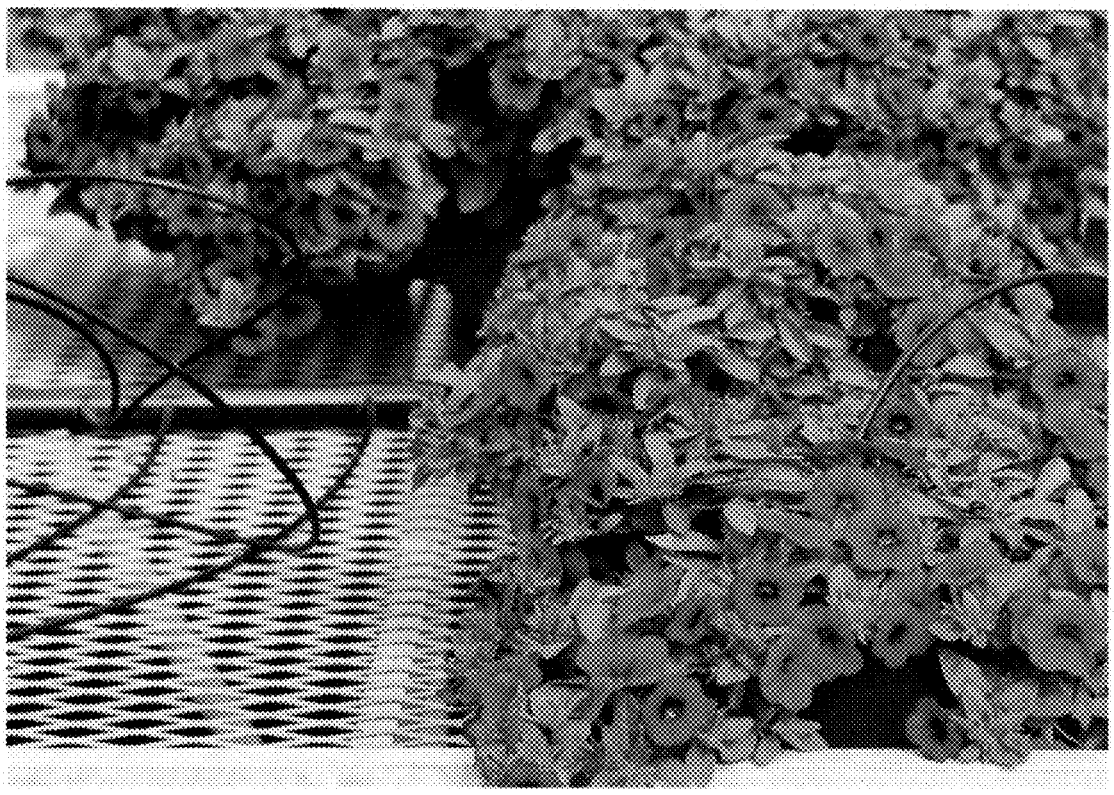
FIG. 2 shows overall plant growth habit.

The following detailed descriptions set forth the distinctive characteristics of 'KLECA09210'. The data which defines these characteristics were collected from asexual reproductions carried out in Stuttgart, Germany. The plant history was taken in May 2009 on 5-month-old plants which were planted as rooted cuttings in a 10 centimeter pot and then grown in a glass greenhouse. The plants had no terminal pinches after potting. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Solanaceae.
- *Botanical*.—*Calibrachoa* sp.
- *Denomination*.—'KLECA09210'.
- *Common*.—*Calibrachoa* hybrid.

Parentage:
- *Female*.—The proprietary *Calibrachoa* plant 'CA060011' (unpatented).
- *Male*.—An unknown individual *Calibrachoa* plant.

Growth:

*Form*.—Semi-trailing.

*Habit*.—Semi-trailing.

*Height* (*measured from the top of the soil*).—6.0 cm.

*Width* (*horizontal plant diameter*).—17.0 cm.

*Time to produce a finished flowering plant*.—9 weeks. Outdoor plant performance: Continuously flowering, healthy, good rain performance.

*Time to initiate and develop roots*.—16 days.

*Root description*.—Moderate density, moderate branching, white roots.

Stems:

*Length of basal branches*.—9.0 cm.

*Internode length*.—2.0 cm.

*Diameter of branches* (*from midpoint*).—5.0 cm to 6.0 cm.

*Color*.—RHS 145B.

*Texture*.—Smooth.

*Anthocyanin*.—No.

*Pedicel*.—Color: RHS 144B. Length: 1.3 cm. Diameter: 0.2 cm. Texture: Smooth.

Leaves:

*Arrangement*.—Alternate.

*Size*.—Length: 2.5 cm to 3.5 cm. Width: 0.9 cm.

*Shape*.—Lanceolate to elliptic.

*Apex*.—Broad acute.

*Base*.—Attenuate.

*Margin*.—Entire.

*Color* (*immature and mature leaves*).—Upper surface: RHS N138B. Lower surface: RHS N138 C.

*Texture* (*both upper and lower surfaces*).—Smooth.

*Venation pattern*.—Pinnate.

*Venation color* (*both upper and lower surfaces*).—RHS 144A.

*Petioles*.—Absent.

Flower bud:

*Shape*.—Irregular to oblong.

*Size*.—Length: 1.5 cm. Diameter: 0.5 cm.

*Color at tight bud*.—RHS N144A.

Inflorescence:

*Blooming habit*.—Continuous flowering during summertime.

*Inflorescence type*.—Single flower, determinate inflorescence.

*Floret type*.—Funnel-shaped, single flower.

*Lastingness of individual blooms on the plant*.—5 days

*Fragrance*.—Absent. .

Flowers:

*Immature flower*.—Diameter: Horizontal: 2.3 cm. Vertical: 2.0 cm. Color: Upper surface: RHS 60C. Lower surface: RHS 64A.

*Mature flower*.—Diameter: Horizontal: 2.8 cm. Vertical: 2.0 cm. Color: Upper surface: RHS 60C. Lower surface: RHS 64A.

*Corolla tube*.—Color inside: RHS 6A. Color outside: RHS 1C. Tube length: 1.0 cm. Texture (outside): Moderate. Texture (inside): Smooth.

*Petals*.—Apex: Obtuse. Base: Open, fused into the tube. Margin: Entire. Waviness of petals: Weak. Lobation: Weak. Texture (both upper and lower surfaces): Smooth.

*Sepals*.—Calyx (composition): Rosette, actinomorphic. Shape: Lanceolate to elliptic. Apex: Acute. Base: Open, tube fused into the base. Margin: Entire. Length: 1.3 cm. Width: 0.3 cm. Color: Upper surface: RHS 138A. Lower surface: RHS 138B. Texture (both upper and lower surfaces): Smooth.

Reproductive organs:

*Stamens*.—Number: 5. Filament color: RHS 154A. Filament length: 0.7 cm. Filament diameter: 0.1 cm. Pollen color: RHS 11A. Pollen quantity: Sparse.

*Pistils*.—Number: 1. Length: 0.3 cm. Diameter: 0.2 cm. Stigma color: RHS 149A.

*Style color*.—RHS 149A.

Fruit and seed set: No fruit or seed set observed.

Disease and insect resistance: No particular resistance or susceptibility has been observed.

COMPARISON WITH PARENTAL AND COMMERCIAL VARIETIES

'KLECA09210' differs from the female parent *Calibrachoa* plant 'CA060011' (unpatented) in that 'KLECA09210' has purple flowers, while 'CA060011' has dark blue flowers.

'KLECA09210' differs from the commercial variety 'MiniFamous Burgundy' (unpatented) in that 'KLECA09210' has more branching and a larger flower size than 'MiniFamous Burgundy'.

We claim:

1. A new and distinct variety of *Calibrachoa* plant named 'KLECA09210' as shown and described herein.

* * * * *